United States Patent
Plenio et al.

(10) Patent No.: US 9,108,996 B2
(45) Date of Patent: Aug. 18, 2015

(54) RUTHENIUM-BASED METATHESIS CATALYSTS AND PRECURSORS FOR THEIR PREPARATION

(71) Applicant: Umicore AG & CO. KG, Hanau (DE)

(72) Inventors: Herbert Plenio, Bensheim (DE); Lars Peeck, Butzbach (DE)

(73) Assignee: UMICORE AG & CO. KG, Hanau (DE)

( * ) Notice: Subject to any disclaimer, the term of this patent is extended or adjusted under 35 U.S.C. 154(b) by 0 days.

(21) Appl. No.: 14/385,100

(22) PCT Filed: Mar. 13, 2013

(86) PCT No.: PCT/EP2013/055160
§ 371 (c)(1),
(2) Date: Sep. 12, 2014

(87) PCT Pub. No.: WO2013/135776
PCT Pub. Date: Sep. 19, 2013

(65) Prior Publication Data
US 2015/0045558 A1    Feb. 12, 2015

(30) Foreign Application Priority Data

Mar. 14, 2012    (EP) .................................... 12159506

(51) Int. Cl.
| | | |
|---|---|---|
| C07F 15/00 | (2006.01) | |
| C07C 211/55 | (2006.01) | |
| C08G 61/08 | (2006.01) | |
| C07D 207/48 | (2006.01) | |
| C07C 67/333 | (2006.01) | |
| B01J 31/18 | (2006.01) | |
| B01J 31/22 | (2006.01) | |
| C07C 67/30 | (2006.01) | |
| C07C 211/54 | (2006.01) | |
| C07D 207/20 | (2006.01) | |

(52) U.S. Cl.
CPC ........... *C07F 15/0046* (2013.01); *B01J 31/181* (2013.01); *B01J 31/2265* (2013.01); *B01J 31/2295* (2013.01); *C07C 67/30* (2013.01); *C07C 67/333* (2013.01); *C07C 211/54* (2013.01); *C07C 211/55* (2013.01); *C07D 207/20* (2013.01); *C07D 207/48* (2013.01); *C08G 61/08* (2013.01); *B01J 2231/543* (2013.01); *B01J 2531/821* (2013.01); *C07C 2101/10* (2013.01); *C08G 2261/418* (2013.01); *C08G 2261/419* (2013.01)

(58) Field of Classification Search
CPC .............. C07F 15/0046; C07C 211/55
See application file for complete search history.

(56) References Cited

U.S. PATENT DOCUMENTS

| 7,329,758 | B1 | 2/2008 | Grubbs et al. |
| 7,820,843 | B2 | 10/2010 | Pederson et al. |
| 2011/0112319 | A1 | 5/2011 | Pederson et al. |

FOREIGN PATENT DOCUMENTS

| WO | 2011/079799 A1 | 7/2011 |
| WO | 2011/091980 A1 | 8/2011 |

OTHER PUBLICATIONS

Cooper et al. CAS Accession No. 1982:122978.*
Cooper et al. "Preparation and characterization of chelating monoolefin-aniline ligands and their platinum(II) complexes" Journal of Organometallic Chemistry, 1981, vol. 221, pp. 231-247.*
Notification of Transmittal of the International Search Report Application No. PCT/EP2013/055160 mailed Jul. 2, 2013.
Cooper, et al. "Preparation and characterization of chelating monoolefin-aniline ligands and their platinum (II) complexes", J. Organometallic Chem. vol. 221, 1981, 231-247.
Zukowska, et al. "Thermal Switchability of N-Chelating Hoveyda-type Catalyst Containing a Decondary Amine Ligand", Organometallics, vol. 31, Jan. 9, 2012, 462-469.
R. Mariz et al. "$C_2$-Symmetric Chrial Disulfoxide Ligands in Rhodium-Catalyzed 1,4 Addition: From Ligand Synthesis to the Enantioselection Pathway" Chem. Eur. J 2010, 16, 14335-14347.
C. Slugovc, D. Butscher, F. Stelzer, K. Mereiter, "Thermally Switchable Olefin Metathesis Initiators Bearing Chelating Carbenes: Influence of the Chelae's Ring Size", Organometallics 2005, 24, 2255-2258.
E. Tzur, A. Szadkowska, A. Ben-Asuly, A. Makal, I. Goldberg, K. Wozniak, K. Grela K, N. G. Lemcoff, "Studies on Electronic Effects in O-, N- and S-Chelated Ruthenium Olefin-Metathesis Catalysts", Chem. Eur. J 2010, 16, 8726-8737.
A. Hejl et al. "Latent Olefin Methathesis Catalysts Featuring Chelating Alkylidens", Organometallics 2006, 25, 6149-6154.
C. E. Diesendruck, E. Tzur, A. Ben-Asuly, I. Goldberg, B. F. Straub, N. G. Lemcoff, "Predicting the Cis-Trans Dichloro Configuration of Group 15-16 Chelaed Ruthenium Olefin Metathesis Complexes: A DFT and Experimental Study", Inorg. Chem. 2009, 48, 10819-10825.

(Continued)

*Primary Examiner* — Joseph Kosack
(74) *Attorney, Agent, or Firm* — Smith, Gambrell & Russell, LLP

(57) ABSTRACT

The invention is directed to ruthenium-based metathesis catalysts of the Hoveyda-Grubbs type. The new N-chelating diarylamino-based ruthenium catalysts described herein are stable in solid state and in solution and reveal rapid initiation behavior. Further, the corresponding N-substituted styrene precursor compounds are disclosed. The catalysts are prepared in a cross-metathesis reaction starting from N-substituted styrene precursors. The new Hoveyda-Grubbs type catalysts are suitable to catalyze ring-closing metathesis (RCM), cross metathesis (CM) and ring-opening metathesis polymerization (ROMP). Low catalyst loadings are sufficient to convert a wide range of substrates via metathesis reactions.

25 Claims, 3 Drawing Sheets

(56) References Cited

OTHER PUBLICATIONS

C. Urbina-Blanco, et al. "Olefin Metathesis Featuring Ruthenium Indenylidene Complexes with a Sterically Demanding NHC Ligand", Chem. Eur. J. 2011, 17, 5045-5053.

A. Szadkowska, X. Gstrein, D. Burtscher, K. Jarzembska, K. Wozniak, C. Slugovc, K. Grela, "Latent Thermo-Switchable Olefin Metathesis Initiators Bearing a Pyridyl-Functionalized Chelating Carbene: Influence of the Leaving Group's Rigidity on the Catalyst's Performance", Organometallics 2010, 29, 117-124.

* cited by examiner

RUTHENIUM-BASED METATHESIS CATALYSTS AND PRECURSORS FOR THEIR PREPARATION

The present invention is directed to ruthenium-based metathesis catalysts of the Hoveyda-Grubbs type. The new N-chelating diarylamino-based ruthenium catalysts described herein are highly stable in solid state and in solution and reveal rapid initiation behavior. In a further aspect, the invention is directed to new styrene-based precursors, which are intermediate products for the preparation of the metathesis catalysts of the present invention. These styrene-based precursors allow a cost-effective and straightforward preparation of the new metathesis catalysts described herein. The invention further provides a method for producing the new catalysts starting from the styrene-based precursors and also relates to the use of the new catalysts for olefin metathesis.

The catalysts are especially suitable to catalyze ring-closing metathesis (RCM), cross metathesis (CM) and ring-opening metathesis polymerization (ROMP). The new family of catalysts combines fast catalyst initiation and high stability with exceptional activity in olefin metathesis reactions. Low catalyst loadings are sufficient to convert a wide range of substrates via metathesis reactions. They allow excellent conversion of a wide range of substrates within short reaction times at low to moderate reaction temperatures.

Ruthenium based catalysts for olefin metathesis reactions are known from the prior art and have gained more and more importance over the past decade. Generally, the olefin metathesis reaction comprises a metal-catalyzed rearrangement of carbon-carbon double bonds and is especially important in the production of complex natural products and polymers. However, such reactions tend to be limited by its initiation rate. Consequently, fast olefin metathesis transformation requires elevated temperatures or rapidly initiating precatalysts.

Ruthenium catalysts are particularly suited for catalyzing such reactions. This is because of their high stability and wide tolerance toward various functional groups. Since their first introduction, these catalysts have been enhanced in their stability and reactivity by various alterations of the respective ligands. For example, Grubbs $3^{rd}$ generation catalysts (ref to formula a) are widely used tools for the production of low dispersity polymers via ring-opening metathesis polymerization (ROMP). However, these complexes have been rarely employed in other metathesis reactions. This may be attributed to the modest stability of the catalysts under elevated reaction conditions.

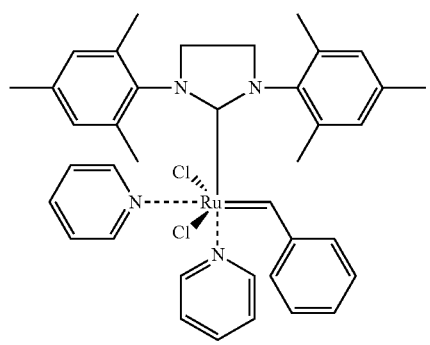

(a)

The initiation rates of the Hoveyda-Grubbs type catalysts of formula (b) known from the prior art are drastically slower compared to Grubbs $3^{rd}$ generation catalysts of formula (a). In a later development, the initiation rates have been slightly improved by replacing hydrogen by a 5-nitro group (formula c).

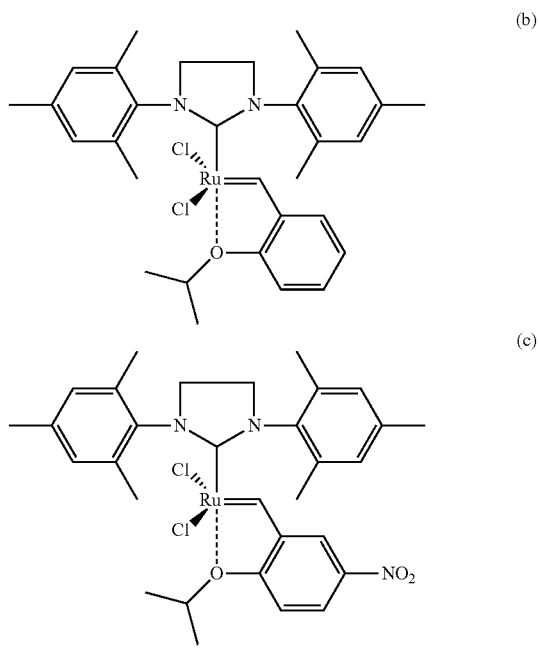

Similar metathesis catalysts with an amine ligand instead of the ether oxygen donor have been reported by Slugovc et al. The reported catalysts with imine functionalities are, however, characterized by very slow initiation rates at room temperature. They can be employed as latent catalysts for ring-opening metathesis polymerization reactions at elevated temperatures around 110° C. (ref. to Slugovc, C., Butscher, D., Stelzer, F., Mereiter, K., *Organometallics* 2005, 24, 2255-2258).

Various olefin metathesis catalysts have also been reported by Lemcoff et al., suggesting oxygen, nitrogen, sulfur, selenium and phosphorus as chelating atoms. Chinoxaline-based catalysts and N,N-Diethyl-derivates have been presented as N-chelating catalysts. However, the activity of these catalysts has not been evaluated (ref. to Diesendruck, C. E., Tzur, E., Ben-Asuly, A., Goldberg, I., Straub, B. F., Lemcoff, N. G., *Inorg. Chem.* 2009, 48, 10819-10825).

Grela et al. have reported pyridine-based ruthenium catalysts bearing a chelating nitrogen atom. The catalysts are stable at ambient conditions and are used to catalyze ring-closing metathesis and ring-opening metathesis polymerizations. The metathesis has been carried out in toluene for 24 to 48 hours with a catalyst loading of 5 mol-% to obtain a sufficient yield at 80° C. A lower catalyst loading led to a significantly decreased conversion (ref. to Szadkowska, A., Gstrein, X., Burtscher, D., Jarzembska, K., Wozniak, K., Slugovc, C., Grela, K., *Organometallics* 2010, 29, 117-124).

Further Hoveyda-Grubbs-type ruthenium catalysts have been prepared by Lemcoff, Tzur et al. The synthesized pyrrolidine-based catalysts showed activity for ring-closing metathesis and cross metathesis. The reaction was carried out in toluene for 24 hours with a catalyst loading of 1 mol-%. A reaction time of 24 hours was necessary for obtaining sufficient yields. After 2 to 6 hours, the yield of the finished product solely amounted to about 24 to 55%. Lower catalyst loadings required a longer reaction time (ref. to Tzur, E., Szadkowska, A., Ben-Asuly, A., Makal, A., Goldberg, I., Wozniak, K., Grela, K., Lemcoff, N. G., *Chem. Eur. J.* 2010, 16, 8726-8737).

Ruthenium catalysts containing an amine chelating ligand have also been reported by Grela et al. (Zukowska, K., Szadkowska, A., Pazio, A. E., Wozniak, K., Grela, K., *Organometallics* 2012, 31, 462-469). These catalysts comprise a chelating nitrogen having a hydrogen atom and an attached group, which may be selected from methyl, benzyl or 4-nitrobenzyl. A high catalyst loading of 1 mol-% or 5 mol-% is used to convert a substrate via ring closing metathesis. Reaction temperatures of 80° C. are necessary for obtaining a sufficiently high yield after reaction times of 6 to 8 hours. The catalysts do not show any notable activity at ambient temperatures. Due to their latency, they reveal a "thermally switchable" behavior and may be employed in syntheses requiring a thermal initiation step.

Accordingly, the catalysts known from the prior art generally have the drawback of slow initiation rates. Thus, elevated reaction temperatures are necessary for obtaining a sufficient yield of the reaction product. Furthermore, reaction times of several hours as well as moderate to high catalyst loadings are, as a rule, necessary to ensure the desired conversion. Thus, catalysts known from the prior art usually have low to moderate activity.

It is one object of the present invention to overcome the drawbacks of the metathesis catalysts known from the prior art. Thus, stable and rapidly initiating Hoveyda-Grubbs type metathesis catalysts are provided by the present invention. Further, new ligand precursors are presented, which are suitable for the synthesis of the catalysts of the present invention. Still further, the invention also provides a method for preparing the new catalysts starting from the corresponding precursors reported herein.

The new Hoveyda-Grubbs type catalysts should be suitable to catalyze olefin metathesis reactions with high yield of final products even at low catalyst loadings. The catalysts should also be capable of catalyzing olefin metathesis reactions under low to moderate temperatures within short reaction times. Thus, the catalysts should possess an increased catalytic activity compared to the activity of catalysts known from the art. The catalyst should be suitable to catalyze different types of olefin metathesis reactions of a broad range of various substrates. Finally, the Hoveyda-Grubbs type catalysts should allow for metathesis reactions under standard inert techniques such as Schlenk techniques without taking special precautions.

The objects of the invention are solved by the subject-matter of the claims. The object is especially solved by the provision of new Hoveyda-Grubbs type catalysts and by the provision of new styrene-based ligand precursors for their preparation.

The catalysts are obtainable starting from the ligand precursors by a cross metathesis reaction with known Ru-benzylidene or Ru-indenylidene complexes in a single-reaction step. This ensures a cost-effective and time-saving preparation route resulting in products with high purity and high yield. The Hoveyda-Grubbs type catalysts of the present invention are especially suitable to catalyze olefin metathesis reactions with a superior activity even at low catalyst loadings and low to moderate temperatures.

The styrene-based precursors for production of the ruthenium-based metathesis catalysts of the present invention are characterized by the formula (I)

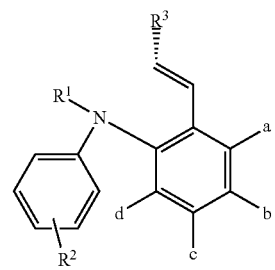

(I)

wherein
- a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
- $R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;
- $R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
- $R^3$ is selected from hydrogen, straight chain or branched $C_1$-$C_{10}$-alkyl groups; and wherein $R^1$ and $R^2$ optionally may form a ring.

Preferably, $R^1$ is a straight chain or branched $C_1$-$C_{10}$-alkyl group. In a further preferred version, $R^1$ is selected from methyl, ethyl, n-propyl, iso-propyl, n-butyl or iso-butyl. In another preferred version, $R^1$ is selected from methyl, ethyl or iso-propyl. In a most preferred embodiment, $R^1$ is a methyl group.

$R^2$ is a substituent at the aryl group. The position of the $R^2$ substituent at the aryl group is not particularly critical. In a preferred embodiment, $R^2$ is hydrogen. In an alternative embodiment, $R^1$ and $R^2$ may form a ring.

EWGs are atoms or functional groups that withdraw electron density from neighboring atoms. Suitable electron-withdrawing groups are selected from halogen atoms, trifluormethyl (—$CF_3$), nitro (—$NO_2$), sulfinyl (—SO—), sulfonyl (—$SO_2$—), formyl (—CHO), $C_1$-$C_{10}$-carbonyl, $C_1$-$C_{10}$-carboxyl, $C_1$-$C_{10}$-alkylamido, $C_1$-$C_{10}$-aminocarbonyl, nitrile (—CN) or $C_1$-$C_{10}$-sulfonamide groups.

$R^3$ is selected from hydrogen or straight chain or branched $C_1$-$C_{10}$-alkyl groups. Preferably, $R^3$ is hydrogen, methyl, ethyl, n-propyl, iso-propyl, n-butyl or iso-butyl. In a most preferred version, $R^3$ is hydrogen or methyl.

Preferably, a, b, c and d are, independently from each other, selected from hydrogen, straight chain or branched alkyl groups including $C_1$-$C_{10}$-alkyl, $C_1$-$C_{10}$-alkoxy or electron-withdrawing groups (EWG). In a preferred embodiment, a, b, c and d each are hydrogen.

According to a further preferred embodiment, the styrene-based precursor for the preparation of the new family of ruthenium-based carbene catalysts is characterized by formula (Ia):

(Ia)

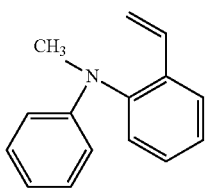

According to an alternative embodiment, the precursor is characterized by formula (Ib):

(Ib)

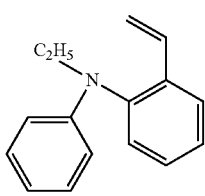

The ortho-vinyl substituted alkyldiphenyl amines are prepared by direct orthometalation with n-BuLi. The new styrene-based precursors may be obtained from the corresponding benzaldehyde intermediates by reaction with Wittig reagent. The reaction conditions are exemplarily presented in the Examples section. The conditions for the preparation of the precursors, in particular of the corresponding benzaldehyde intermediates are well known to a person skilled in the art of preparative organic chemistry.

The Hoveyda-Grubbs type catalysts of the present invention are characterized in that two aryl groups are directly bonded to the chelating nitrogen atom. These new N-chelating diarylamino-based catalysts are described by formula (II):

(II)

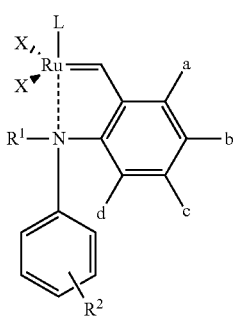

wherein
L is a neutral two-electron donor ligand,
a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
$R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;

$R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
X is an anionic ligand independently selected from the group of halogen anions (i.e. chloride, bromide or iodide), tetrafluoroborate (BEI) or acetate ($CH_3COO^-$);
and wherein $R^1$ and $R^2$ optionally may form a ring.

In this formula, L is representing a neutral two-electron donor ligand. Generally, the neutral two-electron donor ligand is selected from the group of phosphine ligands and the group of N-heterocyclic carbene ligands (NHC ligands). Preferably, the neutral two-electron donor ligand is selected from the group of N-heterocyclic carbene ligands (NHC ligands).

The phosphine ligands may be selected from the group of alkylphosphines such as tri-iso-propylphosphine, tricyclohexylphosphine ($PCy_3$) and tricyclopentylphosphine. Further, the phosphine ligand may be a phospha-bicycloalkane compound such as 9-phosphabicyclo-[3.3.1]nonan or 9-phosphabicyclo-[4.2.1]nonane (also named "phobanes"). Preferably, the phospha-bicycloalkane compound is selected from the group of 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl phobane") and 9-isobutyl-9-phospha-bicyclo-[3.3.1]-nonane ("isobutylphobane").

In a preferred embodiment, L is a N-heterocyclic carbene ligand (NHC ligand). According to the present invention, NHC ligands are N-containing heterocycles comprising stable singlet carbenes that act as excellent two electron donor ligands towards ruthenium. The NHC ligand comprises at least one nitrogen atom and carbon atoms as ring atoms. At least one nitrogen ring atom is bound to a further moiety which is not part of the heterocyclic ring structure. The NHC ligand preferably comprises at least two nitrogen atoms as ring atoms and may be saturated or unsaturated.

The N-heterocyclic carbene ligand is preferably selected from formula (IV) or (V):

(IV)

(V)

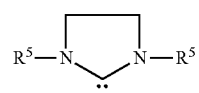

In formula (IV) and (V), $R^5$ is a substituted aryl group selected from 2,4,6-trimethylphenyl ("mesityl"), 2,6-di-isopropylphenyl, 3,5-di-tert.-butylphenyl and 2-methylphenyl and combinations thereof.

Preferably, the NHC ligand is selected from the group of 1,3-bis-(2,4,6-trimethylphenyl)-imidazolidine-2-ylidene ("SIMes"), 1,3-bis-(2,6-diisopropylphenyl)-imidazolidine-2-ylidene ("SIPr") or 1,3-bis-(2,6-diisopropylphenyl)-imidazoline-2-ylidene (unsaturated NHC, "IPr").

X is an anionic ligand, preferably from the group of halogen anions such as chloride, bromide or iodide; in a most preferred embodiment, X is Cl⁻.

The substituents $R^1$, $R^2$ as well as the groups a, b, c and d and the EWG substituents are defined as described above for the styrene-based precursor of formula (I). Preferably, $R^1$ is a straight chain or branched $C_1$-$C_{10}$-alkyl group. In a further preferred version, $R^1$ is selected from methyl, ethyl, n-propyl, iso-propyl, n-butyl or iso-butyl. In another preferred version, $R^1$ is selected from methyl, ethyl or iso-propyl. In a most preferred embodiment, $R^1$ is a methyl group. $R^2$ is a substituent at the aryl group. The position of the $R^2$ substituent at the aryl group is not particularly critical. In a preferred embodiment, $R^2$ is hydrogen. In an alternative embodiment, $R^1$ and $R^2$ may form a ring.

$R^3$ is selected from hydrogen or straight chain or branched $C_1$-$C_{10}$-alkyl groups. Preferably, $R^3$ is hydrogen, methyl, ethyl, n-propyl, iso-propyl, n-butyl or iso-butyl. In a most preferred version, $R^3$ is hydrogen or methyl.

Preferably, a, b, c and d are, independently from each other, selected from hydrogen, straight chain or branched alkyl groups including $C_1$-$C_{10}$-alkyl, $C_1$-$C_{10}$-alkoxy or electron-withdrawing groups (EWG). In a further preferred embodiment, a, b, c and d each are hydrogen.

In a specific embodiment, the N-chelating diarylamino-based catalyst is characterized by formula (IIa):

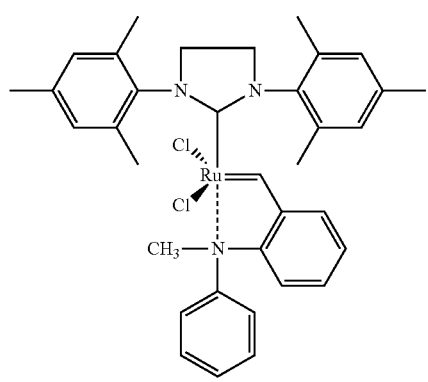

(IIa)

In a further specific embodiment, the N-chelating diarylamino-based catalyst is characterized by formula (IIb):

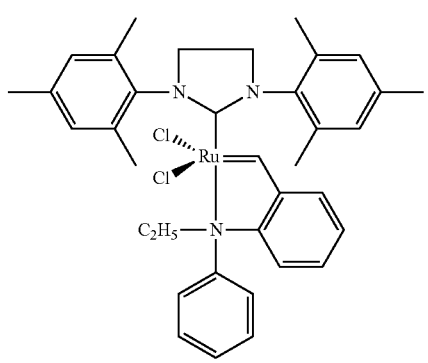

(IIb)

In further specific embodiments, the N-chelating diarylamino-based catalysts are characterized by formula (IIc) and formula (IId):

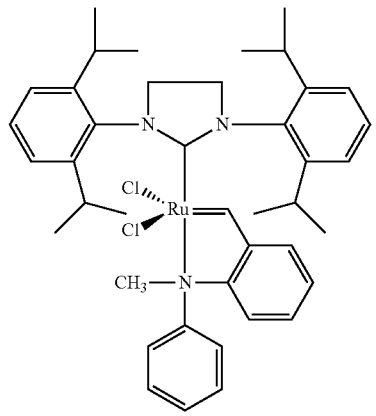

(IIc)

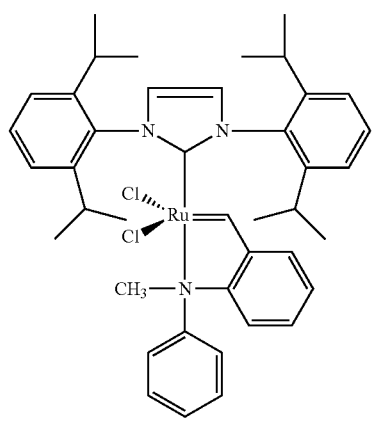

(IId)

In addition to the N-chelating diarylamino-based Ru-catalyst described above, the present invention also refers to a method for manufacturing these new catalysts. Generally, the present catalysts are obtainable from the new precursors of formula (I) via a single-step reaction. A single step reaction according to the present invention is a reaction that precedes without necessitating intermediate isolation or intermediate purification steps (one-pot synthesis).

A variety of Ru-based starting complexes of the general formula $L_2X_2Ru=CR_xR_y$ (wherein $R_x$ and $R_y$ may be independently hydrogen, alkyl or aryl and wherein $R_x$ and $R_y$ may form a ring) can be employed as starting material for the preparation of the catalysts of the present invention. Examples of suitable Ru-based starting complexes are the well-known Ru-benzylidene complexes of Grubbs 1st generation (containing phosphine ligands) or the Grubbs 2nd generation Ru-complexes (containing NHC ligands).

In a preferred method of the invention, the precursor of formula (I) is reacted with a Ru-phenylindenylidene complex of formula (III) in a cross metathesis reaction to obtain the catalysts of formula (II). This reaction is shown in scheme 1.

Scheme 1

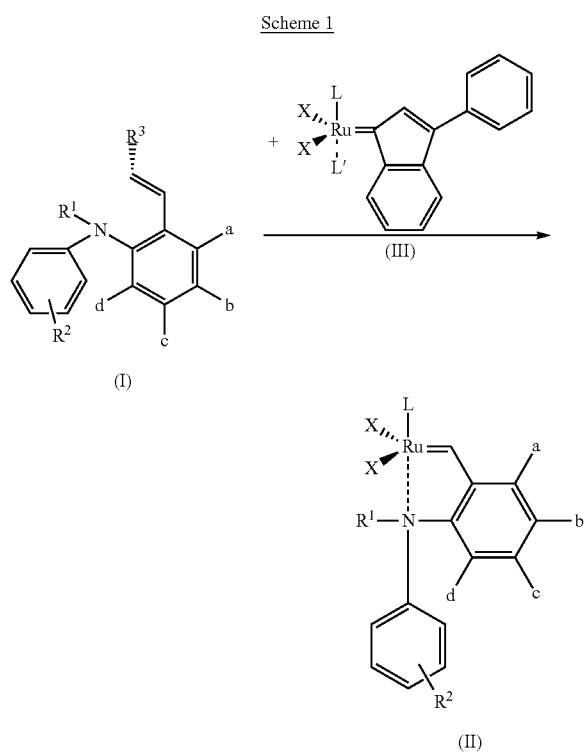

In the Ru-starting complex of formula (III), L may be a phosphine ligand selected from the group of tri-isopropylphosphine, tricyclohexylphosphine (PCy$_3$), tricyclopentylphosphine and phospha-bicycloalkane compounds such as 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl phobane") and 9-isobutyl-9-phospha-bicyclo-[3.3.1]-nonane ("isobutylphobane").

In a preferred version of the method, Lisa NHC ligand selected from the group of 1,3-bis-(2,4,6-trimethylphenyl)-imidazolidine-2-ylidene ("SIMes"), 1,3-bis-(2,6-di-isopropylphenyl)-imidazolidine-2-ylidene ("SIPr") or 1,3-bis-(2,6-diisopropylphenyl)-imidazoline-2-ylidene (unsaturated NHC, "IPr").

Further, in the Ru-starting complex of formula (III) above, L' is a leaving ligand representing a phosphine ligand selected from the group of triisopropylphosphine, tricyclohexylphosphine (PCy$_3$), tricyclopentylphosphine, 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl phobane"), 9-isobutyl-9-phospha-bicyclo-[3.3.1]-nonane ("isobutylphobane") or a pyridine ligand, which may be substituted or unsubstituted. Examples are pyridine or bromo-pyridine.

X is an anionic ligand, preferably from the group of halogen anions such as chloride, bromide or iodide; in a most preferred embodiment, X is Cl$^-$.

Depending on the Ru-starting complexes used, the reaction conditions for the cross metathesis reaction may be modified; in particular, Cu-salts (such as CuCl or CuBr) may be added as phosphine scavengers when using phosphine containing Ru-starting complexes such as, for example, (PCy$_3$)$_2$Cl$_2$Ru-phenylindenylidene. It should be noted, however, that the addition of Cu-salts is not necessary, if the leaving ligand L' is not a phosphine.

In a further preferred version of the method, Ru-starting complexes with leaving ligands L'=pyridine (py) may be employed, such as for example (SIMes)(py)RuCl$_2$(3-phenyl-indenylid-1-ene) [Umicore M31] or (SIPr)(py)RuCl$_2$(3-phenylindenylid-1-ene) [Umicore M32]. To facilitate the formation of the desired complexes, the pyridine ligand can be removed by in-situ protonation with a protic ion exchange resin (according to the method described in WO2011/091980). Further improved yields are obtained.

The cross metathesis reaction may be conducted in chlorinated hydrocarbon solvents such as dichloromethane (DCM), chloroform or 1,2-dichloroethane (DCE) or in cyclic ethers such as tetrahydrofurane (THF) or dioxane. Alternatively, aromatic hydrocarbon solvents such as benzene or toluene as well as esters and mixtures of the listed solvents may be employed. Most preferably, purified toluene is used as reaction solvent.

The suitable reaction time depends on the type of the starting materials. Typically, the reaction times are in the range of 0.5 to 4 hours, preferably 0.5 to 2 hours and most preferably 0.5 to 1.5 hours. Reaction temperatures may vary depending on the raw materials. Typically, reaction temperatures in the range of 50 and 100° C., preferably in the range of 50 to 80° C. are appropriate. Temperatures in the range of 65 to 80° C. are particularly preferred, as, in some cases, the formation of the corresponding cis-dichloro isomer of the catalyst (having lower catalytical activity compared to the trans-isomer) can be avoided. The reaction is preferably carried out under an inert gas such as nitrogen or argon.

After stirring the reaction mixture for a given period of time, the reaction solvent is removed preferably in vacuo. The remaining reaction mixture may be further purified. This is preferably done by column chromatography. The resulting product may be re-crystallized from a non-polar hydrocarbon solvent for obtaining the Ru-catalyst with high purity. The non-polar hydrocarbon solvent may be selected from n-pentane, cyclohexane, n-hexane, n-heptane or mixtures thereof. The resulting catalyst is separated, preferably by filtration. Further purification steps may be conducted. The product may, for example, be washed with a non-polar hydrocarbon solvent. Generally, the Ru-catalysts of the present invention can be obtained with good yields in high purity.

The N-chelating diarylamino ruthenium catalysts may be used to catalyze metathesis reactions with a wide range of substrates. As already described, these catalysts are particularly suitable to catalyze ring-closing metathesis (RCM), cross metathesis (CM), ring-opening metathesis polymerization (ROMP) and other metathesis reactions. In general, metathesis reactions are performed in homogenous phase. Alternatively, the reaction may be carried out in a heterogeneous manner with immobilized or supported catalysts; for example in the presence of a cation-exchange resin. The reaction conditions for the metathesis reactions are well known to a person skilled in the art. The reaction is carried out in a suitable reaction solvent, which may be, for example, dichloroethene, hexafluorobenzene or toluene. Preferably the reaction solvent comprises toluene. Most preferably the organic solvent is toluene. Preferably, the metathesis reaction is conducted under a protective inert gas such as nitrogen or argon.

The Ru-catalysts of the present invention enable reaction temperatures below 60° C. As shown in the Examples section, the reaction temperature may be lowered to 20 to 30° C.; these temperatures are already sufficient for complete conversion. Such low temperatures are important when employing temperature-sensitive substrate materials.

Further, the Ru-catalysts of the present invention enable low catalyst loadings. In some reactions, the catalyst loading does not exceed 1.000 ppm, i.e. 0.1 mol-%. Catalyst loadings lower than 250 ppm, preferably lower than 100 ppm have been found sufficient for obtaining high conversions while ensuring a cost-effective metathesis reaction.

The Ru-catalysts of the present invention allow metathesis reactions with short reaction times. Typically, as shown in the Experimental section, more than 65% of the substrate is converted after 15 minutes. This is measured by known methods, preferably by gas chromatography (GC). In most cases a conversion of 70% and preferred of 75% is obtained with the catalysts of the present invention after a reaction time of at least 15 minutes under the conditions mentioned above. In various metathesis reactions, the conversion reaches 93% or even 95% after 15 minutes reaction time. In some cases, a yield of isolated finished product of >88%, more preferably ≥90% can be obtained.

The catalysts of the present invention show a fast initiation rate and thus trans-late into fast and efficient olefin metathesis reactions while having an excellent catalytic activity. A TON ("Turn-over number"; i.e. molar ratio of converted substrate to catalyst) of preferably $>5 \times 10^3$, preferably $>8 \times 10^3$ and most preferably $>1 \times 10^4$ may be obtained with the inventive new family of catalysts. The TOF (TON per hour; turn-over frequency) which is a measure for the catalytic activity amounts up to $>1 \times 10^4$ h$^{-1}$, preferably $>8 \times 10^4$ h$^{-1}$ and most preferably $>1 \times 10^5$ h$^{-1}$.

It was found, that it is necessary to provide the right balance between the steric and electronic effects of the substituents bonded to the chelating nitrogen atom in order to tailor the activity of the catalysts of the present invention. Thus it is supposed that the excellent activity of the catalysts compared to the ruthenium-based catalysts of formula (b) and (c) may result from the specific basicity of the chelating nitrogen atom due to the aryl moiety attached to the N-atom. This modification in the nature of the N-donor atom in the benzylidene amine ligand may contribute to a weakening of the Ru—N interaction and consequently lead to a significant increase in the initiation rate of the catalyst. Up to date, such N-chelating diarylamino-Ru catalysts have not been described in the literature.

In summary, the catalysts of the present invention combine fast catalyst initiation and high stability with exceptional activity in olefin metathesis reactions. Low catalyst loadings are sufficient to obtain excellent yields of final products even within short reaction times and at low to moderate reaction temperatures.

As the new catalysts are obtainable with high purity and high yield from new precursors in a one-step reaction, they can be produced economically in industrial scale.

Figure 1:
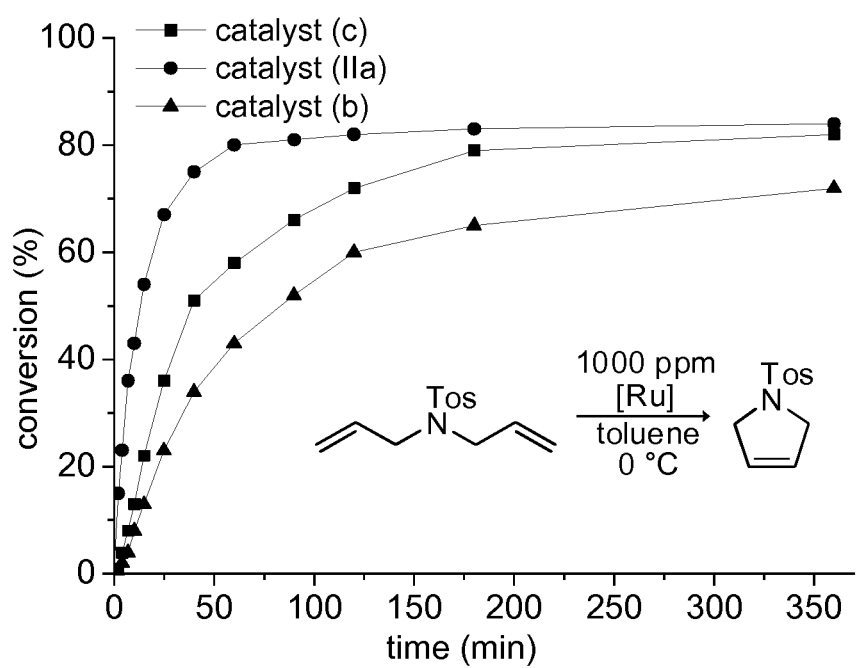
FIG. 1 shows the conversion (in %) of diallyl-N-tosylamide (0.1 mol/L) during RCM reaction of 0° C. in toluene using 0.1 mol-% (1.000 ppm) of catalysts of formulas (IIa), (b) and (c).

The invention is further described by the following Examples without limiting or narrowing the scope of protection.

EXAMPLES

General Remarks

All chemicals were purchased as reagent grade from commercial suppliers and used without further purification, unless otherwise noted. All reactions involving Ruthenium complexes were performed under an atmosphere of nitrogen. $CH_2Cl_2$ (99.5) and pentane (99) were obtained from Gruessing GmbH, toluene from Sigma-Aldrich (Lab. Reagent grade, 99.3%). These solvents were dried and degassed by using a column purification system. In this system, the solvents are sparged and pressurized with argon (0.1 to 1 bar), followed by successive passing through a column filled with activated alumina and a second column, either filled with a supported copper catalyst (toluene, pentane) or again activated alumina ($CH_2Cl_2$). Toluene was additionally dried over $CaH_2$ and distilled onto molecular sieves (3 Å). Tetrahydrofuran was dried over sodium and distilled onto molecular sieves (3 Å). $^1H$ and $^{13}C$ nuclear magnetic resonance spectra were recorded with a Bruker DRX300 spectrometer. The chemical shifts are given in parts per million (ppm) on the delta scale (δ) and are referenced to tetramethylsilane ($^1H$-, $^{13}C$-NMR=0 ppm) or the residual peak of $CHCl_3$ ($^1H$-NMR=7.26 ppm, $^{13}C$-NMR=77.16 ppm). Abbreviations for NMR data: s=singlet; d=doublet; t=triplet; q=quartet; sep=septet; m=multiplet; bs=broad signal; Ar=aromatic protons.

UV-Vis spectrophotometric data were acquired on an Analytik Jena SPECORD S 600 UV-Vis spectrophotometer. Thin layer chromatography (TLC) was performed using silica gel 60 F 254 (0.2 mm) on aluminium plates. Preparative chromatography E. Merck silicagel 60 (0.063-0.02 mesh).

GC experiments were run on a Glarus 500 GC with autosampler and FID detector. Column: Varian CP-Sil 8 CB (l=15 m, $d_i$=0.25 mm, $d_F$=1.0 lm), $N_2$ (flow: 17 cm s$^{-1}$; split 1:50); Injector-temperature: 270° C., detector temperature: 350° C. The following compounds were prepared according to literature procedures: 2-(N-phenyl)-aminobenzaldehyde, diethyl 2,2-diallylmalonate, N,N-diallyl-4-methylbenzene-sulfonamide.

Example 1

Preparation of the Precursor (Ia)

The preparation of the new precursors is exemplarily described for the precursor of formula (Ia).

a) 2-(N-methyl-N-phenyl)-aminobenzaldehyde

In a 100 mL Schlenk flask, 2-(N-phenyl)-aminobenzaldehyde (0.41 g, 2.08 mmol) was dissolved in dry and degassed DMF (20 mL). $Cs_2CO_3$ (2.71 g, 8.32 mmol) was added and the suspension was stirred at room temperature. After 2 hours methyl iodide (0.52 mL, 8.32 mmol) was added and the reaction mixture was stirred overnight. Deionized water (20 mL) was added and the mixture was extracted with diethyl ether (3×50 mL). The organic phase was dried over $MgSO_4$ and concentrated in vacuo. The crude product was purified by column chromatography (cyclohexane/ethyl acetate 20:1+ 1% NEt$_3$). Yield: 0.41 g (93%), yellow solid. $^1H$ and $^{13}C$-NMR data were in accordance with published data.

b) 2-(N-methyl-N-phenyl)-aminostyrene

In a 100 mL Schlenk flask, MePPh$_3$I (3.14 g, 7.8 mmol) and KOtBu (0.88 g, 7.8 mmol) were suspended in dry and degassed THF (10 mL) at 0° C. The mixture was stirred for 2 hours and allowed to warm to room temperature. Thereafter, the mixture was cooled to −60° C. (iPrOH/N$_2$(I)) and a solution of 2-(N-methyl-Nphenyl)aminobenzaldehyde (0.41 g, 1.9 mmol) in dry and degassed THF (5 mL) was added. The mixture was stirred over night, during which it was allowed to warm to ambient temperature. Silica (15 mL) was added to the reaction mixture and the solvent was removed in vacuo. Purification via column chromatography (cyclohexane/ethyl acetate 20:1 v/v+1% NEt$_3$) afforded the desired product as a colorless oil. Yield: 0.36 g (91%). The colorless oil has been analyzed via $^1$H-NMR (500 MHz, CDCl$_3$) and $^{13}$C-NMR (126 MHz, CDCl$_3$) and HRMS.

$^1$H-NMR (500 MHz, CDCl$_3$): δ 7.72 (d, J=7.0 Hz, 1H, o-ArH), 7.49-7.07 (m, 5H, ArH), 6.98-6.71 (m, 2H, ArH+ArCH=CH$_2$), 6.65 (d, J=7.9 Hz, 2H, o-ArH), 5.79 (d, J=17.7 Hz, 1H, ArCH=CHcisHtrans), 5.27 (d, J=11.0 Hz, 1H, ArCH=CHcisHtrans), 3.25 (s, 3H, NCH$_3$).

$^{13}$C-NMR (126 MHz, CDCl$_3$): δ 149.6, 146.4, 136.3, 133.2, 129.5, 129.0, 128.6, 126.6, 126.5, 117.3, 115.3, 113.5, 39.8.

HRMS: m/z calcd for C$_{15}$H$_{15}$N: 209.1205. found: 209.11775.

Example 2

Preparation of Catalyst (IIa)

To a solution of 2-(N-methyl-N-phenyl)aminostyrene (70 mg, 0.32 mmol) in toluene (2.5 mL) was added [(SIMes)(py)RuCl$_2$(3-phenylindenylid-1-ene)] (200 mg, 0.27 mmol; Umicore M31, Umicore AG & Co KG, Hanau) and the mixture was stirred for 120 min at 75 C. The mixture was concentrated in vacuo and purified by column chromatography (cyclohexane/acetone 7:1 v/v+0.5% NEt$_3$). The obtained product was recrystallized from cyclohexane, yielding the desired complex as a green microcrystalline solid. The obtained product has been analyzed via $^1$H-NMR (300 MHz, CDCl$_3$), $^{13}$C-NMR (75 MHz, CDCl$_3$) and HRMS.

R$_F$(cyclohexane/acetone 7:1 v/v+0.5% NEt$_3$)=0.15.

$^1$H-NMR (300 MHz, CDCl$_3$): δ 17.00 (s, 1H, RuCH), 7.59 (td, J=8.0, 1.5 Hz, 1H), 7.30 (d, J=8.0 Hz, 1H, o-ArH), 7.19 (td, J=7.5, 1.0 Hz, 1H, m-ArH), 7.13-6.88 (m, 8H, ArH), 6.80-6.70 (m, 2H, ArH), 4.07 (s, 4H, NCH$_2$CH$_2$N), 2.91 (s, 3H, NCH$_3$), 2.79-1.70 (m, 18H, o-ArCH$_3$).

$^{13}$C-NMR (75 MHz, CDCl$_3$): δ 299.2, 210.3, 208.5, 155.8, 151.4, 146.5, 139.2, 138.9, 138.6, 129.5, 129.4, 129.3, 127.9, 127.4, 126.9, 123.5, 122.0, 121.1, 53.8, 51.7, 21.3, 19.5.

Analytical data for C$_{35}$H$_{39}$Cl$_2$N$_3$Ru:
Calculated: C, 62.40; H, 5.84; N, 6.24.
Found: C, 62.53; H, 5.95; N, 5.96.

Example 3

Preparation of Catalyst (IIb)

[(SIMes)(py)RuCl$_2$(3-phenylindenylid-1-ene)] (150 mg, 0.2 mmol; Umicore M31) was charged into a Schlenk flask and toluene (2.5 mL) was added under an atmosphere of argon. The mixture was heated to 50° C. and 2-(N-ethyl-N-phenyl)aminostyrene 42 mg, 0.18 mmol) was added. The mixture was stirred for 3 h at 50° C. After this, the solvent was removed in vacuo and the remaining solid purified by column chromatography (short column, ethyl acetate/cyclohexane, 1:5, v/v). The obtained product was treated with pentane and the resulting suspension was cooled to −35° C. The product was collected by filtration and washed with cold pentane and dried in vacuo. The obtained product has been analyzed via $^1$H-NMR (300 MHz, CDCl$_3$), $^{13}$C-NMR (75 MHz, CDCl$_3$).

$^1$H-NMR (300 MHz, CDCl$_3$): δ=16.93 (s, 1H, Ru=CH), 7.53 (t, J=7.4 Hz, 1H), 7.33 (d, J=7.9 Hz, 1H), 7.17 (t, J=7.3 Hz, 2H), 7.12-7.01 (m, 5H), 7.01-6.88 (m, 5H), 4.05 (s, 4H, NCH$_2$CH$_2$N), 3.69-3.49 (m, 1H, CH$_a$H$_b$CH$_3$), 2.95-2.75 (m, 1H, CH$_a$H$_b$CH$_3$), 2.68-2.09 (m, 18H, CH$_3$), 0.55 (t, J=6.8 Hz, 3H, CH$_2$CH$_3$).

$^{13}$C-NMR (75 MHz, CDCl$_3$): δ=300.60, 210.53, 196.57, 157.83, 148.00, 143.93, 139.14 (br.), 138.68 (br.), 138.52, 129.56, 129.30, 128.68, 127.60, 127.02, 123.24, 121.31, 121.01, 56.77, 51.66, 21.31, 19.55 (br.), 11.24.

Example 4

Preparation of Catalyst (IIc)

A Schlenk tube containing [(SIPr)(py)RuCl$_2$(3-phenylindenylid-1-ene)] complex (150 mg, 0.18 mmol; Umicore M32, Umicore AG & Co KG, Hanau) was evacuated and back-filled with argon three times. Toluene (1.66 ml), n-hexane (0.83 ml) and 2-(N-methyl-N-phenyl)aminostyrene (=N-methyl-N-phenyl)-2-vinylaniline; 41.4 mg, 0.198 mmol) in toluene (2.5 mL) were added under an atmosphere of argon. The mixture was heated at 70° C. for 120 min. Volatiles were removed in vacuo and the residue was purified by column chromatography (cyclohexane/EtOAc, 4:1 v/v). The product was treated with pentane (3 ml) and the suspension was cooled to −35° C. After filtration and washing with cold pentane the desired complex is obtained as microcrystalline green solid. The compound was characterized by $^1$H- and $^{13}$C-NMR spectroscopy.

Example 5

Preparation of Catalyst (IId)

A Schlenk tube containing [(IPr)(py)RuCl$_2$(3-phenylindenylid-1-ene)] complex (150 mg, 0.18 mmol) was evacuated and back-filled with argon three times. Toluene (1.66 ml), n-hexane (0.83 ml) and (N-methyl-N-phenyl)-2-vinylaniline (41.4 mg, 0.198 mmol) in toluene (2.5 mL) were added under an atmosphere of argon. The mixture was heated at 70° C. for 120 min. Volatiles were removed in vacuo and the residue was purified by column chromatography (cyclohexane/EtOAc, 5:1 v/v). The product was treated with pentane (3 ml) and the suspension was cooled to −35° C. After filtration and washing with cold pentane the desired complex is obtained as microcrystalline green solid. The compound was characterized by $^1$H- and $^{13}$C-NMR spectroscopy.

Catalyst Testing

The new catalysts have exemplarily been evaluated in ring-closing metathesis reactions (RCM). Furthermore, the activity has been compared with precatalysts known from the prior art, i.e. catalysts of formulas (b) and (c) shown above.

Results of Ring-Closing Metathesis (RCM)

Catalysts of formulas (IIa), (IIb), (IIc) were systematically tested for a number of ring closing metathesis reactions leading to N-heterocycles. A comparison with prior art catalysts ((b) and (c)) was made.

The ring-closing reactions have been carried out in toluene at 50° C. with a reaction time of 15 min. The substrate was present in an amount of 0.5 mol/L with the exception of example no. 2 (here the substrate concentration is 0.1 mol/L). Reactions were carried out in sealed 10 mL Schlenk tubes under an atmosphere of argon at 50° C. In a 10 mL Schlenk tube, substrate was dissolved in dry toluene (2 mL) under an atmosphere of argon. This solution was heated to 50° C. and the catalysts were added from a stock solution (e.g. formula (IIa): [Ru]=3.0 mmol/L or 0.75 mmol/L) in toluene. For the determination of substrate conversion, samples (50 µL) were taken after the specified times under a stream of argon. The samples were injected into gas chromatography vials containing 250 µL of a 25% (v/v) ethyl vinyl ether solution in toluene and analyzed by gas chromatography. The products were isolated via column chromatography (silica) using mixtures of pentane/diethyl ether as eluent. The degree of conversions is the average conversion of two runs. The results are presented in Table 1. The tested catalysts allow excellent conversion (≥65%) of the substrates, using catalyst loadings between 25 and 200 ppm. Thereby, catalysts of formulas (IIa) and (IIc) turned out to be more efficient than (IIb). In comparison to prior art catalysts (b) and (c), the catalysts of the present invention show improved activity in RCM and various other metathesis reactions.

TABLE 1

Conversion (in %) in RCM reactions of various substrates for catalysts of the invention (IIa, IIb, IIc) and prior art catalysts (b) and (c) at different catalyst loadings

| Entry | Substrate | Catalyst loading [ppm] | Conversion (%) | | | | |
|---|---|---|---|---|---|---|---|
| | | | (b) | (c) | IIa | IIb | IIc |
| 1 | diallyl-N-tosylamide | 25 | 70 | 61 | 84 | 71 | 98 |
| 2 | bis-homoallyl-N-tosylamide | 100 | 67 | 76 | 82 | — | 93 |
| 3 | diethyl diallylmalonate (DEDAM) | 200 | 29 | 65 | 84 | 67 | 97 |

Reaction conditions: Toluene solvent, 0.5M substrate, T = 50° C., reaction time 15 mins, conversions detected by GC, average of two runs.

Apart from the low catalyst loading the short time required for such reactions is most notable all of the reactions studied are completed within less than 15 min.

TON and TOF have been calculated for substrate no. 1 and a catalyst loading of 25 ppm. Accordingly, by using catalyst (IIa) a TON of $3.6 \times 10^4$ and a TOF of $1.3 \times 10^5$ $h^{-1}$ has been observed. This is a significant improvement with respect to the prior art.

Comparative Tests with Prior Art Catalysts

The initiation rates of the catalyst of formula (IIa) as well as the catalysts of formula (b) and (c) known from the art at various olefin concentrations (di-ethyldiallylmalonate; DEDAM) were determined according to a method reported by Plenio et al. (Vorfalt, T., Wannowius, K. J., Plenio, H., *Angew. Chem., Int. Ed.* 2010, 49, 5533-5536). The initiation process was monitored by recording UV/Vis spectra to follow the spectral changes with time.

In the RCM of diallyl-N-tosylamide at 0° C. precatalyst of formula (IIa) is significantly faster than the prior art catalysts (b) and (c). At low temperatures fast initiation translates into excellent catalytic activities compared to catalysts (b) and (c) known from the art, which initiate considerably more slowly. FIG. 1 shows the results of the RCM reaction.

Figure 2:
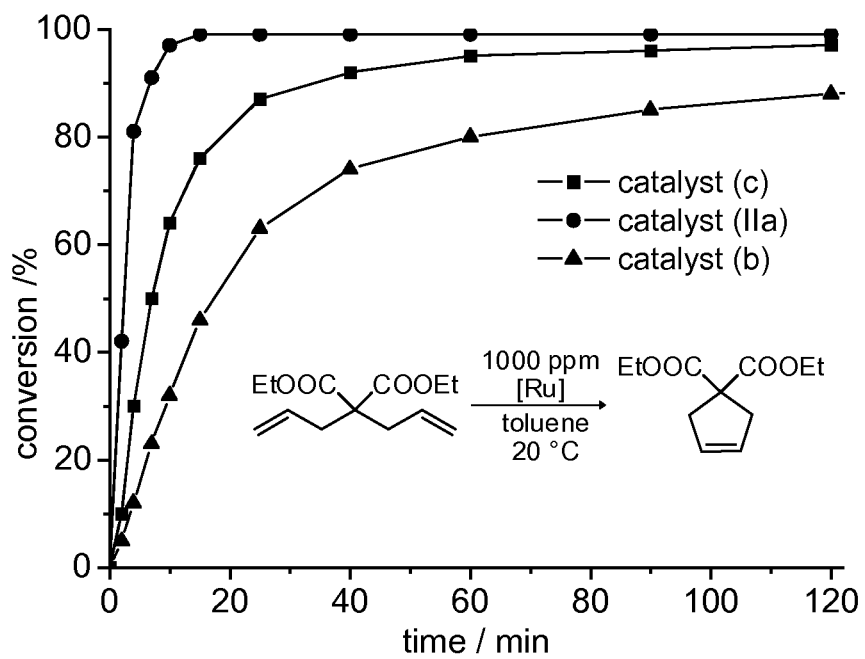
FIG. 2 shows the conversion (in %) of DEDAM (0.1 mol/L) at 20° C. in toluene using 1.000 ppm of catalysts of formulas (IIa), (b) and (c).
Figure 3:
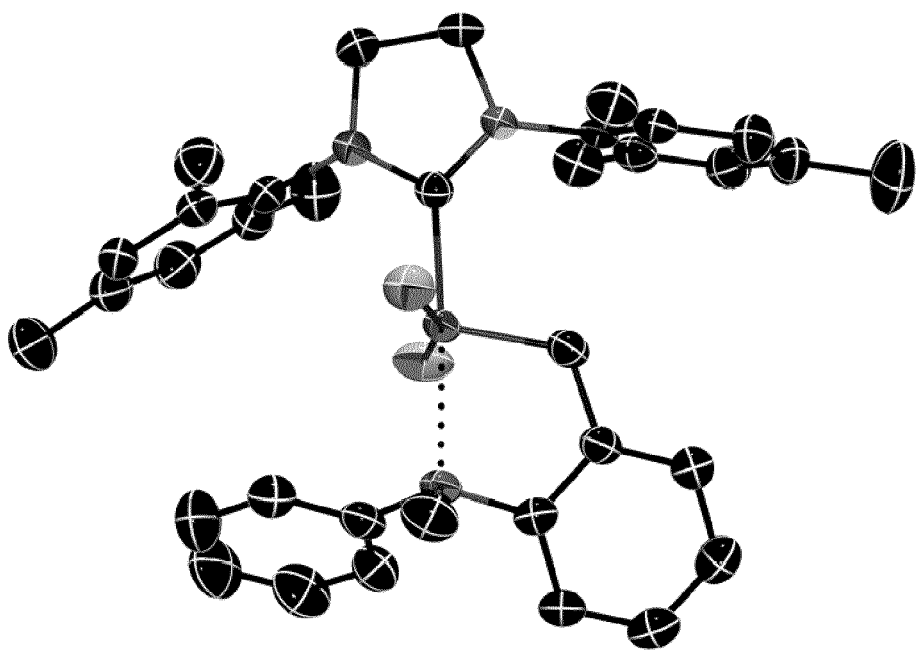
FIG. 3 shows an ORTEP plot of the crystal structure of complex (IIa). Important bond lengths (μm) and angles (°) are: Ru—N 234.7(4), Ru—CHAr 182.6(5), Ru—C(NHC) 201.4 (5), Ru—Cl 234.0(1), 235.0 (1), Cl—Ru—Cl 162.58 (6), N—Ru—C(NHC) 175.53 (15).

The ability of the catalyst of formula (IIa) to rapidly catalyze RCM reactions is also apparent for DEDAM reactions. In FIG. 2, the results of the RCM reaction of DEDAM in toluene using 1.000 ppm of catalysts of formulas (IIa), (c) and (b) are presented. With catalyst of formula (IIa) full substrate conversion is achieved within about 10 min, while catalyst of formula (c) requires roughly ten times longer and catalyst of formula (b) does not appear to reach full conversion. These results demonstrate that the main advantage of the catalyst of formula (IIa) is the short time required for the RCM transformations.

Furthermore, a strong influence of temperature on the catalyst performance has been noted. In order to obtain about 84% yield in the RCM of diallyl-N-tosylamide at 0° C., about 1.000 ppm of the catalyst of formula (IIa) are required at a reaction time of 120 min. At 50° C. the same yield is obtained within 15 min using only 25 ppm of the catalyst of formula (IIa) (ref to Table 1).

Comparative Tests with Prior Art Catalyst Containing a Secondary Amine Ligand

Ruthenium catalysts containing a secondary amine chelating ligand have been reported by Grela et al. (Zukowska, K., Szadkowska, A., Pazio, A. E., Wozniak, K., Grela, K., *Organometallics* 2012, 31, 462-469). As outlined in the introductionary section of this application, these catalysts comprise a chelating secondary amine group having a hydrogen atom and an attached alkyl group, which may be selected from methyl, benzyl or 4-nitrobenzyl.

To demonstrate the improved reactivity of the catalysts of the present invention vs. these prior art catalysts, a further comparative test was conducted, involving a ring closing metathesis reaction (RCM) of substrate 2-methallyl-allyldiethylmalonate.

Catalyst IIa (according to the present invention) was employed in a catalyst loading of 100 ppm (0.01 mol-%) in toluene solvent at a substrate concentration of c=0.5 mol/L. After a reaction time of 15 minutes at a reaction temperature of 50° C., a substrate conversion of 95% was obtained (determined by GC, average over 2 runs).

For the RCM reaction with the identical substrate (methallyl-allyldiethylmalonate), Grela et al. reported a conversion of 45% after a reaction time of 8 hours using the N-chelating Hoveyda-type catalyst 15c (containing a secondary amine with a benzyl group and a SIMES ligand) in a catalyst loading of 5 mol-% and a substrate concentration of c=0.1 mol/L (ref to Grela et al, section 2.2., Table 2, entry V, pages 464-465, paper cited above). As the other reaction conditions (solvent, temperature) are identical, these results underline the high reactivity, in particular the rapid initiation behavior of the N-chelating diarylamino-based ruthenium catalysts of the present invention. Low catalyst loadings are sufficient to convert a wide range of substrates in metathesis reactions within short reaction times.

The invention claimed is:

1. Compound of formula (I) for the preparation of ruthenium-based catalysts

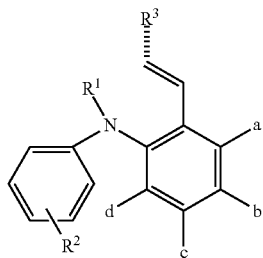

wherein
- a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
- $R^1$ is selected from straight chain or branched $C_1$-$C_{10}$-alkyl, $C_1$-$C_{10}$-alkoxy, $C_1$-$C_{10}$-alkylcarbonyl, or $C_5$-$C_6$-cycloalkyl;
- $R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
- $R^3$ is selected from hydrogen, straight chain or branched $C_1$-$C_{10}$-alkyl groups;
- and wherein $R^1$ and $R^2$ optionally may form a ring.

2. Compound according to claim 1, wherein the electron-withdrawing groups are selected from halogen atoms, trifluoromethyl (—$CF_3$), nitro (—$NO_2$), sulfinyl (—SO—), sulfonyl (—$SO_2$—), formyl (—CHO), $C_1$-$C_{10}$-carbonyl, $C_1$-$C_{10}$-carboxyl, $C_1$-$C_{10}$-alkylamido, $C_1$-$C_{10}$-aminocarbonyl, nitrile (—CN) or $C_1$-$C_{10}$-sulfonamide.

3. Compound according to claim 1, wherein
- a, b, c and d each are hydrogen;
- $R^1$ is methyl, ethyl, n-propyl, iso-propyl, n-butyl or iso-butyl;
- $R^2$ is hydrogen;
- $R^3$ is hydrogen, methyl, ethyl, n-propyl, iso-propyl, n-butyl or iso-butyl.

4. Compound according to claim 3, having the formula (Ia)

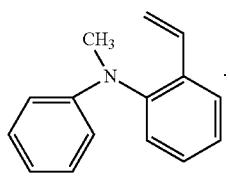

5. Compound according to claim 3, having the formula (Ib)

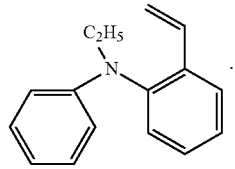

6. Ruthenium-based catalyst of formula (II)

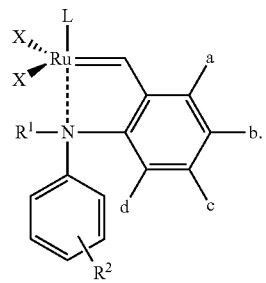

wherein
- L is a neutral two-electron donor ligand selected from a phosphine ligand or a N-heterocyclic carbene (NHC) ligand,
- a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
- $R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;
- $R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
- X is an anionic ligand independently selected from the group of halogen anions ($Cl^-$, $Br^-$, $I^-$), tetrafluoroborate ($BF_4^-$) or acetate ($CH_3COO^-$);
- and wherein $R^1$ and $R^2$ optionally may form a ring.

7. Catalyst according to claim 6, wherein the electron-withdrawing groups are selected from halogen atoms, trifluormethyl (—$CF_3$), nitro (—$NO_2$), sulfinyl (—SO—), sulfonyl (—$SO_2$—), formyl (—CHO), $C_1$-$C_{10}$-carbonyl, $C_1$-$C_{10}$-carboxyl, $C_1$-$C_{10}$alkylamido, $C_1$-$C_{10}$-aminocarbonyl, nitrile (—CN) or $C_1$-$C_{10}$-sulfonamide.

8. Catalyst according to claim 6, wherein L is a N-heterocyclic carbene (NHC) ligand.

9. Catalyst according to claim 6,
wherein L is a N-heterocyclic carbene ligand having the formula (IV) or (V)

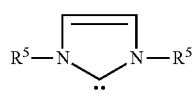

(IV)

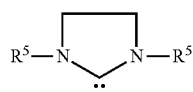

(V)

wherein

R⁵ is selected from the group of 2,4,6-trimethylphenyl, 2,6-di-isopropyl-phenyl, 3,5-di-tert.-butylphenyl, 2-methylphenyl and combinations thereof.

10. Catalyst according to claim 6, wherein

L is a NHC ligand selected from the group of 1,3-bis-(2,4,6-trimethylphenyl)-imidazolidine-2-ylidene ("SIMes"), 1,3-bis-(2,6-di-isopropylphenyl)-imidazolidine-2-ylidene ("SIPr") or 1,3-bis-(2,6-di-isopropylphenyl)-imidazoline-2-ylidene ("IPr");

X is $Cl^-$;

a, b, c and d each are hydrogen;

$R^1$ is methyl, ethyl, n-propyl, iso-propyl, n-butyl or iso-butyl;

$R^2$ is hydrogen.

11. Catalyst according to claim 6, wherein L is a phosphine ligand selected from the group of tri-isopropylphosphine, tricyclohexylphosphine ($PCy_3$), tricyclopentylphosphine and phospha-bicycloalkane compounds selected from the group of 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane ("2,2,4-trimethylpentyl phobane") and 9-isobutyl-9-phospha-bicyclo-[3.3.1]-nonane ("isobutylphobane").

12. Catalyst according to claim 10, having the formula (IIa)

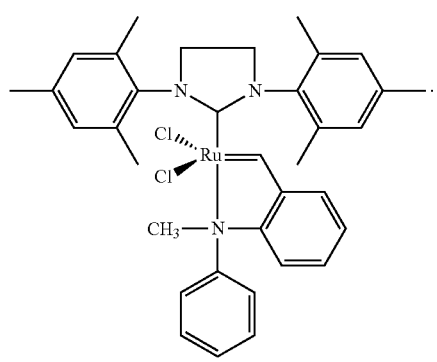

(IIa)

13. Catalyst according to claim 10, having the formula (IIb)

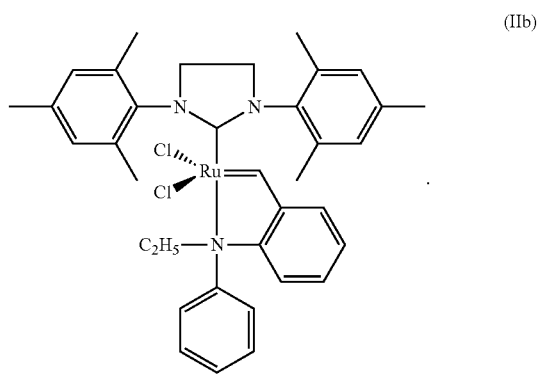

(IIb)

14. Catalyst according to claim 10, having the formula (IIc)

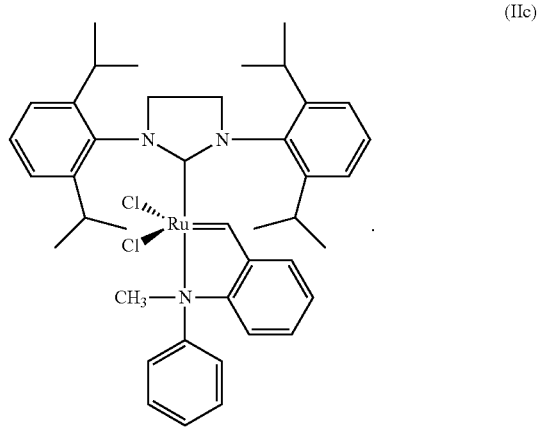

(IIc)

15. Catalyst according to claim 10, having the formula (IId)

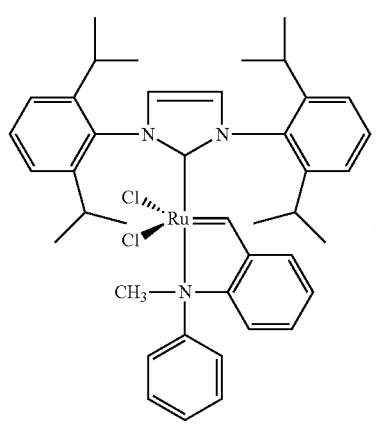

(IId)

16. Method for preparing a ruthenium-based catalyst of formula (II)

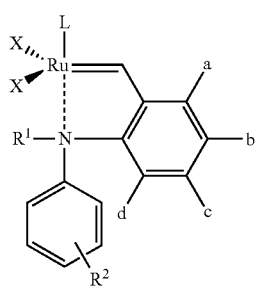

(II)

wherein
  L is a neutral two-electron donor ligand selected from a phosphine ligand or a N-heterocyclic carbene (NHC) ligand,
  a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
  $R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;
  $R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
  X is an anionic ligand independently selected from the group of halogen anions ($Cl^-$, $Br^-$, $I^-$), tetrafluoroborate ($BF_4^-$) or acetate ($CH_3COO^-$);
  and wherein $R^1$ and $R^2$ optionally may form a ring,
the method comprising reacting the compound of claim 1 with a Ru-starting compound having the formula (III):

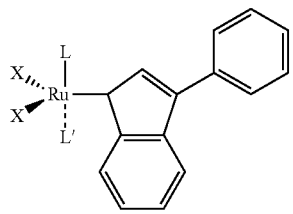

(III)

in a cross metathesis reaction,
wherein
  L' is a leaving ligand selected from the group of tri-isopropylphosphine, tricyclohexylphosphine (PCy3), tricyclopentylphosphine, cyclo-hexyl-phoban, 2,2,4-trimethylpentyl-phobane, isobutyl-phoban or substituted or un-substituted pyridines.

17. Method for preparing a ruthenium-based catalyst of formula (II)

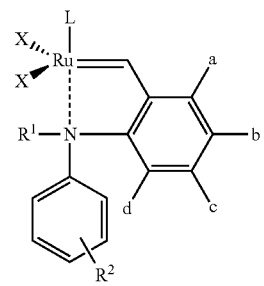

(II)

wherein
  L is a neutral two-electron donor ligand selected from a phosphine ligand or a N-heterocyclic carbene (NHC) ligand,
  a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
  $R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;
  $R^2$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);
  X is an anionic ligand independently selected from the group of halogen anions ($Cl^-$, $Br^-$, $I^-$), tetrafluoroborate ($BF_4$) or acetate ($CH_3COO^-$);
  and wherein $R^1$ and $R^2$ optionally may form a ring,
the method comprising reacting the compound of claim 1 with a Ru-starting compound having the formula (III):

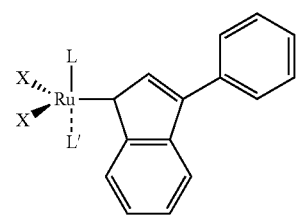

(III)

in a cross metathesis reaction,
wherein
  L' is pyridine.

18. A method for olefin metathesis, comprising: utilizing the catalyst according to claim 6 in the olefin metathesis, wherein the olefin metathesis comprises ring-closing metathesis (RCM), cross metathesis (CM) or ring-opening metathesis polymerization (ROMP).

19. A method for olefin metathesis, comprising: utilizing the catalyst according to claim 6 in the olefin metathesis, wherein the olefin metathesis is carried out at temperatures <55° C. with catalyst loadings <0.1 mol-%.

20. A method for ring-closing metathesis (RCM), comprising: utilizing the catalyst according to claim 6 in the ring-closing metathesis (RCM), wherein the activity of the catalyst in the reaction (turn-over frequency, TOF) is $>1\times10^4$ $h^{-1}$.

21. Compound of formula (I) for the preparation of ruthenium-based catalysts

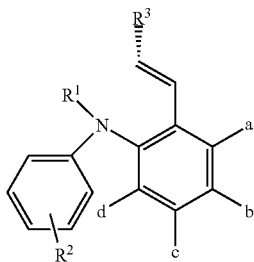

(I)

wherein
a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);

$R^1$ is selected from straight chain or branched $C_1$-$C_{10}$-alkyl, $C_1$-$C_{10}$-alkoxy, $C_1$-$C_{10}$-alkylcarbonyl, $C_5$-$C_6$-cycloalkyl or $C_6$-$C_{14}$-aryl groups;

$R^2$ is selected from straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_6$-$C_{14}$-aryl, $C_6$-$C_{14}$-aryloxy, $C_6$-$C_{14}$-heterocyclic or electron-withdrawing groups (EWG);

$R^3$ is selected from hydrogen, straight chain or branched $C_1$-$C_{10}$-alkyl groups;

and wherein $R^1$ and $R^2$ optionally may form a ring.

22. The method of claim 16, wherein L, in formula (III), is a phosphine ligand selected from tri-iso-propyl-phosphine, tricyclohexylphosphine ($PCy_3$), tricyclopentyl-phosphine, cyclohexyl-phoban, 2,2,4-trimethylpentyl phobane or isobutylphoban or a NHC ligand selected from 1,3-bis-(2,4,6-trimethylphenyl)-imidazolidine-2-ylidene ("SIMes"), 1,3-bis-(2,6-di-isopropylphenyl)-imidazolidine-2-ylidene ("SIPr"), or 1,3-bis-(2,6-di-isopropylphenye-imidazoline-2-ylidene ("IPr").

23. The method of claim 16, wherein X, in formula (III), is an anionic ligand selected from Cl–, Br–, or I–.

24. The method of claim 17, wherein L, in formula (III), is a NHC ligand selected from 1,3-bis-(2,4,6-trimethylphenyl)-imidazolidine-2-ylidene ("SIMes"), 1,3-bis-(2,6-di-isopropylphenyl)-imidazolidine-2-ylidene ("SIPr"), or 1,3-bis-(2, 6-di-isopropylphenyl)-imidazoline-2-ylidene ("IPr").

25. The method of claim 17, wherein X, in formula (III), is $Cl^-$.

* * * * *